United States Patent
Cohen et al.

(10) Patent No.: US 10,682,525 B2
(45) Date of Patent: Jun. 16, 2020

(54) SYSTEMS, APPARATUSES, AND METHODS FOR ULTRAVIOLET (UV) TREATMENT

(71) Applicants: Emil I. Cohen, Arlington, VA (US); Lori E. Cohen, Arlington, VA (US)

(72) Inventors: Emil I. Cohen, Arlington, VA (US); Lori E. Cohen, Arlington, VA (US)

(*) Notice: Subject to any disclaimer, the term of this patent is extended or adjusted under 35 U.S.C. 154(b) by 687 days.

(21) Appl. No.: 15/154,310

(22) Filed: May 13, 2016

(65) Prior Publication Data
US 2016/0331996 A1    Nov. 17, 2016

Related U.S. Application Data

(60) Provisional application No. 62/162,088, filed on May 15, 2015.

(51) Int. Cl.
*A61B 18/18* (2006.01)
*A61N 5/06* (2006.01)
*A61L 2/10* (2006.01)

(52) U.S. Cl.
CPC ............. *A61N 5/0624* (2013.01); *A61L 2/10* (2013.01); *A61N 5/0616* (2013.01); *A61L 2202/11* (2013.01); *A61L 2202/14* (2013.01); *A61N 2005/0626* (2013.01); *A61N 2005/0651* (2013.01); *A61N 2005/0661* (2013.01)

(58) Field of Classification Search
CPC ............. A61N 5/0616; A61N 5/0624; A61N 2005/0626; A61N 2005/0651; A61N 2005/0661; A61L 2/10; A61L 2202/11; A61L 2202/14
USPC ..................................... 607/88, 94
See application file for complete search history.

(56) References Cited

U.S. PATENT DOCUMENTS

| | | | |
|---|---|---|---|
| 6,053,180 A | 4/2000 | Kwan | |
| 7,409,954 B2 | 8/2008 | Dobkine et al. | |
| 7,834,328 B2 | 11/2010 | Redmond et al. | |
| 8,241,258 B2 | 8/2012 | Pelkus | |
| 8,668,727 B2 | 3/2014 | Natale et al. | |
| 2003/0153962 A1* | 8/2003 | Cumbie | A61L 2/10 607/94 |
| 2006/0241729 A1 | 10/2006 | Dawson | |
| 2008/0234786 A1 | 9/2008 | Cumbie | |
| 2008/0306454 A1 | 12/2008 | Sikora | |
| 2009/0149922 A1 | 6/2009 | White | |
| 2010/0121420 A1* | 5/2010 | Fiset | A61N 5/06 607/94 |
| 2011/0152751 A1 | 6/2011 | Dacey et al. | |

(Continued)

FOREIGN PATENT DOCUMENTS

| | | |
|---|---|---|
| DE | 102007034174 A1 | 1/2009 |
| WO | WO 2009/065128 A2 | 5/2009 |
| WO | WO 2013/138449 A1 | 9/2013 |

OTHER PUBLICATIONS

"Development of UV-LED Disinfection." TECHNEAU (Feb. 2010), 36 pages.

(Continued)

*Primary Examiner* — Aaron F Roane
(74) *Attorney, Agent, or Firm* — Moazzam & Associates, LLC

(57) ABSTRACT

Aspects disclosed herein include systems, apparatuses, and methods for administration of a one or more wavelengths of UVA light in an effective amount to an area/target for reducing pathogen growth.

15 Claims, 6 Drawing Sheets

(56) References Cited

U.S. PATENT DOCUMENTS

2012/0053512 A1 3/2012 Muse
2014/0105784 A1* 4/2014 Smeeton ............... B01J 19/123
422/24
2017/0100871 A1 4/2017 Fukuda

OTHER PUBLICATIONS

Hamamoto, et al., "New water disinfection system using UVA light-emitting diodes." Journal of Applied Microbiology (2007); 103(6): 2291-2298.
Lazcka, et al., "Pathogen detection: A perspective of traditional methods and biosensors." Biosensors and Bioelectronics (2007); 22(7): 1205-1217.
Lowe, et al., Sunscreens: Development: Evaluation, and Regulatory Aspects: Second Edition, CRC Press (1996); pp. 110-113, 6 pages.
Magill, et al., "Multistate Point-Prevalence Survey of Health Care—Associated Infections." N Engl J Med (2014); 370: 1198-1208.
Robson, et al., "Rapid bacterial screening in the treatment of civilian wounds." Journal of Surgical Research (1973); 14(5): 426-430.
Singh et al., "Recent Advances in Bacteriophage Based Biosensors for Food-Borne Pathogen Detection." Sensors (2013); 13(2): 1763-1786.
Ultraviolet Radiation Guide, Navy Environmental Health Center (1992), online at <http://www.med.navy.mil/sites/nmcphc/Documents/policy-and-instruction/ih-ultraviolet-radiation-technical-guide.pdf>, downloaded Feb. 15, 2018, 21 pages.
Ye, et al., "Disinfection Using UVA Light on Glass Surfaces with or without Titanium Dioxide Coating." 2011 5th International Conference on Bioinformatics and Biomedical Engineering.

* cited by examiner

SYSTEMS, APPARATUSES, AND METHODS FOR ULTRAVIOLET (UV) TREATMENT

CROSS-REFERENCE TO RELATED PATENT APPLICATION

This application claims priority to U.S. Application No. 62/162,088, filed May 15, 2015, and entitled "SYSTEMS, APPARATUSES, AND METHODS FOR ULTRAVIOLET (UV) TREATMENT," the disclosure of which is incorporated herein by reference in its entirety.

TECHNICAL FIELD

The present disclosure is directed to systems, apparatuses, and methods for reduction or elimination of pathogenic (bacterial or otherwise) growth on a skin defect and/or on a device entering the body for medical therapy by utilizing a specific range of ultraviolet (UV) light in the 315-400 nm, range (also known as "UVA" light), such as in the 365-370 nm range.

BACKGROUND

Prevention and treatment of skin infections has been, and continues to be, important. Each year 41,000 central line-associated bloodstream infections (CLABSI) occur within US hospitals (see Centers for Disease Control and Prevention CLABSI Report 2012, incorporated herein by reference). There are two common routes of pathogenic colonization of the bloodstream during catheter use: through the skin defect that was created for the catheter, and/or through the catheter lumen itself. These catheters, generally known as tunneled and non-tunneled central venous lines, are used both for administration of medication or alimentation as well as withdrawal of blood samples for monitoring the patient. See FIG. 1.

Similarly, skin defects created by surgical procedures can also carry a risk of infection. Each year more than 150,000 such infections occur within acute care hospitals. (Magill, S. S., et al., "Multistate point-prevalence survey of health care-associated infections". New England Journal of Medicine, 370(13): (2014): 1198-208). Bacterial growth in the surgical wound, even in the absence of an overt infection, can slow or inhibit the healing process (Granick, M. S. & Teot, L. *Surgical Wound Healing and Management, Second Edition*, CRC Press, 2012).

A random sampling of post-surgical wounds demonstrated that 20% of them have at least 100,000 organisms per gram of tissue (Robson, M. C., Duke, W. F., and Krizek, T. J. (1973). Rapid bacterial screening in the treatment of civilian wounds. Journal of Surgical Research 14, 426-430). Furthermore, both types of infections can be prevented to a large extent.

Methods used to reduce catheter related infections can include: 1) impregnation of the catheter with antibacterial agents, such as silver sulfadiazine; 2) placement of chlorhexidine gluconate (CHG) impregnated discs at the level of the catheter-related skin defect (has been shown to reduce infections by as much as 69%); 3) frequent flushing of the catheter with saline solutions; 4) placement of alcohol caps at the luer locks of the catheter; as well as other methods.

Each of these methods can reduce infections, but due to the wide spread use of these catheters both in the acute setting as well as their long term use in areas such as hemodialysis, CLABSI costs thousands of lives and millions of dollars annually. In addition, each of theses methods has drawbacks, not the least of which is cumulative additive costs as well as staff time for their deployment.

Radiation can inhibit the growth of microorganisms through inhibition of normal cellular mechanisms either through direct interaction with DNA or through creation of intermediaries such as oxygen radicals. UV radiation, specifically, is used in numerous fields ranging from water and food treatment to medical equipment sterilization.

The various wavelengths of ultraviolet (UV) light fall in three categories: UVA (near UV) 315-400 nm, UVB (middle UV) 280-315 nm, and UVC (far UV) 180-280 nm.

It is known that UVB and UVC have antibacterial properties. In previous work on the utility of UVB for treatment of water, treatment with 100 $J/m^2$ (or 10 $mW/cm^2$) of UVB resulted in an almost 100 fold reduction of bacterial growth. The dose-response curve obtained was logarithmic (Techneau, Development of UV-LED Disinfection, February 2010, and Hamamoto, A. et al. New water disinfection system using UVA light-emitting diodes. *Journal of Applied Microbiology* 103, 2291-2298 (2007), incorporated herein by reference in its entirety).

UVB and UVC hence have been utilized in the above fields because they directly damage DNA of organisms but UVA, despite its better penetration profile, has not been used as a sole option for the inhibition of microorganism growth. In comparison to UVB and UVC, UVA is characterized by a longer wavelength with better penetration profile. There is significant loss of the shorter wavelengths even in normal oils or at most the top epidermis skin layer (Ultraviolet Radiation Guide. (1992) found online at <http://www.med-.navy.mil/sites/nmcphc/Documents/policy-and-instruction/ih-ultraviolet-radiation-technical-guide.pdf> Ultraviolet Radiation Guide, incorporated herein by reference). It has been generally agreed upon that UVA is not, by itself, effective in controlling bacterial populations (Ye, L., Martinez, S. G., Swain, L., Zhao, Z. & Moller, K. Disinfection Using UVA Light on Glass Surfaces with or without Titanium Dioxide Coating. in (*iCBBE*) 2011 *5th International Conference on Bioinformatics and Biomedical Engineering* 1-3 (2011). doi:10.1109/icbbe.2011.5780340, incorporated herein by reference). UVA is not well absorbed by DNA but it can produce free radicals which can damage multiple pathways important for maintenance of biological function of microorganisms. Table 1 (Ye, L., Martinez, S. G., Swain, L., Zhao, Z., and Moller, K. (2011). Disinfection Using UVA Light on Glass Surfaces with or without Titanium Dioxide Coating. In (iCBBE) 2011 5th International Conference on Bioinformatics and Biomedical Engineering, pp. 1-3) illustrates how combined utilization of Titanium Oxide and UVA significantly reduced bacterial growth. The control column illustrates that there was a significant drop in *S. aureus* and *E. faecium* as well as the fungus *Candida*, a common human fungal infection.

TABLE 1

Inactivation of various bacteria by photocatalysis on TiO$_2$-coated Plexiglas ® with UVA light (60 min)

| Germ | Multi-plicity | Initial germ count ± error (CFU/ml) | Final germ count ± error (CE in CFU/ml) | | Control final germ count ± error (CCE in CFU/ml) | Reduction efficiency |
|---|---|---|---|---|---|---|
| E. coli | 3 | $1.2 \times 10^7 \pm 0.09 \times 10^7$ | <5 | — | $1.1 \times 10^7 \pm 0.13 \times 10^7$ | >6.3 |
| P. aeruginosa | 4 | $1.5 \times 10^6 \pm 0.12 \times 10^6$ | <5 | — | $1.2 \times 10^6 \pm 0.22 \times 10^6$ | >5.4 |
| S. aureus | 2 | $0.8 \times 10^5 \pm 0.15 \times 10^5$ | <5 | — | $4.3 \times 10^6 \pm 2.6 \times 10^4$ | >3.9 |
| E. faecium | 4 | $3.6 \times 10^7 \pm 0.36 \times 10^7$ | $1.3 \times 10^2$ | $2.5 \times 10^4$ | $1.6 \times 10^7 \pm 0.51 \times 10^7$ | 3.1 |
| C. albicans | 3 | $1.1 \times 10^5 \pm 0.08 \times 10^5$ | $4.1 \times 10^3$ | $6.2 \times 10^3$ | $6.2 \times 10^6 \pm 1.1 \times 10^4$ | 1.2 |

Reduction efficiencies (RE) = log$_{10}$ (CCE − CE); CE = number of viable cells in CFU/ml after irradiation; CCE = number of viable cells of the control in CFU/ml after irradiation; error: at multiplicity n ≥ 3; standard deviation of the mean; at n < 3: error = ½ × (value 1 − value 2).

SUMMARY

Embodiments of the present invention include apparatus, systems, and methods of UV treatment to reduce pathogenic growth. In one example, a method of reducing pathogen growth on a target area is disclosed. The method includes applying an effective amount of UVA light on the target area. In another example, a method of sterilizing a target is disclosed. The method includes applying, to the target, an effective amount of UVA light.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1:
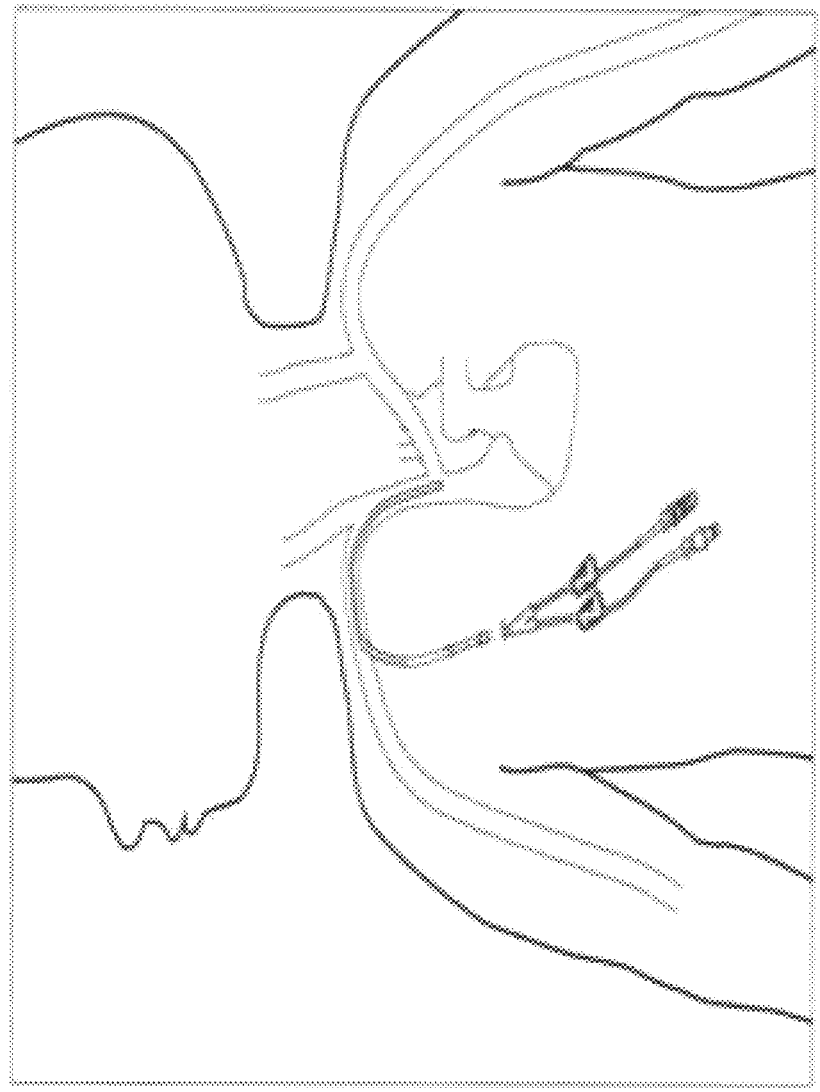
FIG. 1 illustrates a use of catheters for administration of medication or alimentation as well as withdrawal of blood samples for monitoring the patient.

Aspects disclosed herein include systems, apparatuses, and methods for administration of a one or more wavelengths of UVA light in an effective amount to an area/target for reducing and/or inhibiting pathogen growth. In some embodiments, aspects disclosed herein are directed to systems, apparatuses, and methods for reducing/inhibiting pathogen growth in an area, such as a skin defect, with or without the presence of a catheter.

In some embodiments, a UVA light emitting diode (LED) can be utilized as the source for emission of the desired spectrum. In some embodiments, the amount of energy to be deposited can be calculated to yield substantially no growth of pathogens. In some embodiments, the deposited energy can be based on a targeted reduction of the growth rate. In some embodiments, substantial elimination of pathogenic growth may not be necessary, as the immune system can handle most pathogens in small numbers.

In some embodiments, aspects of the systems, apparatuses and method disclosed herein can include incorporation into another device, such as, for example, a dressing overlying a skin access site for a central venous catheter. The system and/or apparatus can include a LED, a programmable and/or pre-programmed control circuit/device (also referred to as a "circuit board"), and a power source. In some embodiments, depending on use, the system and/or apparatus can be configured to emit a relatively higher dose of UVA if it is being exposed to a medical device such as a catheter, or a relatively lower dose of UVA if being exposed to a wound. In some embodiments, the circuit board can be programmed with preset operating conditions for the system and/or apparatus.

In some embodiments, the system and/or apparatus includes a catheter that incorporates an LED, power source and circuit board. During use of the catheter for skin insertion, the LED, power source and board can be proximal to the skin insertion site.

In some embodiments, multiple LEDs can be electronically linked to form an LED source (e.g., in a row, or as an array of LEDs), and their output can be controlled by a circuit board. In some embodiments, the system and/or apparatus, or at least a portion thereof, is flexible and can be altered in form so as to, for example, conform to a wound (surgical or otherwise). In some embodiments, the system and/or apparatus can include an adhesive component that can be configured to, for example, adhere to a wound (surgical or otherwise). The LEDs can emit light simultaneously or in various sequences.

Aspects disclosed herein are directed to systems, apparatuses, and methods of treating, disinfecting, and/or sterilizing by reducing and/or eliminating pathogenic growth, and can include delivering an effective amount of UVA light to a target.

In some embodiments, systems, apparatuses, and methods for treating a condition of a patient are disclosed. The condition can include, but is not limited to, skin infections, such as staph infections, leprosy, carbuncles, cellulitis, impetigo, boils, pilonidal cyst, fungal skin infections, ringworms, athlete's foot, candidiasis, sporotrichosis, fungal nail infections, and/or the like. For example, common staph infections can be caused by common skin flora such as *Staphylococcus aureus, Staphylococcus pyogenes,* and *Staphylococcus epidermis* (Cunha), and can further lead to bacteremia if left untreated.

In some embodiments, systems, apparatuses, and methods for disinfecting a target are disclosed. The target can include, but is not limited to, skin defects, and the infection can include, but is not limited to, infection caused by *Staphylococcus aureus, Pseudomonas aeruginosa, Escherichia coli, Staphylococcus epidermidis, Enterococcus faecalis* (Giacometti et al.), combinations thereof, and/or the like.

In some embodiments, systems, apparatuses, and methods for sterilizing a target are disclosed. The target can include, but is not limited to, skin surfaces, oral surfaces, surgical instruments, central venous catheters, intravenous lines (IV's), wound dressings, and/or the like.

In some embodiments, the systems and/or apparatuses disclosed herein include at least a processor and a memory, such as, for example, formed on a circuit board as disclosed herein. In some embodiments, the system and/or apparatus can include one or more UVA sources, and a controller (e.g., a controller including a processor and a memory, such as a circuit board), and optionally, a power source.

UVA light can be any light having a wavelength between 315-400 nm, including all values and ranges in between. In some embodiments, the wavelength can be between about 365-370 nm. Sources of UVA light that can be employed include, but are not limited to, UV-LEDs, such as Gallium Nitride (GaN) LEDs, Aluminum Nitride (AlN) LEDs, and/or the like.

The UVA light can be delivered substantially continuously, or in a pulsed manner, or both. In some embodiments, continuous delivery can be relatively more effective at reducing bacterial growth, such as, for example, on surgical instruments and/or other non-biological targets. In some embodiments, such as in the case of biological targets, since continuous delivery can result in relatively greater power consumption and unwanted energy deposition in the adjacent structures, pulsed delivery can be additionally and/or alternatively employed to optimize portability/durability of the device and/or minimize the risks of unwanted energy deposition in adjacent structures of biological targets.

An 'effective amount' of UVA light can be any amount that reduces pathogen viability at the target area/site of treatment. In some embodiments, the effective amount of UVA can be defined in terms of the intensity incident on the target area (e.g., when the UVA light source is in continuous wave (CW) mode). In some embodiments, the effective amount of UVA can be about 1 mW/cm$^2$ of the target area, about 1.5-mW/cm$^2$, about 1.8 mW/cm$^2$, about 2 mW/cm$^2$, about 2.4 mW/cm$^2$, about 2.8 mW/cm$^2$, about 3.2 mW/cm$^2$, about 3.6 mW/cm$^2$, about 4.0 mW/cm$^2$, about 4.5 mW/cm$^2$, about 5 mW/cm$^2$, about 10 mW/cm$^2$, about 20 mW/cm$^2$, about 30 mW/cm$^2$, about 40 mW/cm$^2$, about 45 mW/cm$^2$, about 50 mW/cm$^2$, about 56 mW/cm$^2$, including all values and sub ranges in between. In some embodiments, the effective amount of UVA is about 3.6 mW/cm$^2$, at which (see Example 4) a near complete absence of growth can be achieved. It is understood that many variables can affect bacterial growth and the effective amount of UVA required, including (but not limited to) surface type, temperature, humidity, and competing microorganisms.

In some embodiments, the effective amount of UVA can be defined in terms of the energy density incident on the target area (e.g., when the UVA light source is in pulsed mode). In some embodiments, the effective amount of UVA can be about 5 J/cm$^2$ of the target area, about 8 J/cm$^2$, about 10 J/cm$^2$, about 12 J/cm$^2$, about 13 J/cm$^2$, about 14 J/cm$^2$ about 16 J/cm$^2$ about 18 J/cm$^2$ about 20 J/cm$^2$ about 22 J/cm$^2$ about 24 J/cm$^2$ about 26 J/cm$^2$ about 30 J/cm$^2$, about 35 J/cm$^2$, about 40 J/cm$^2$ about 45 J/cm$^2$, including all values and sub ranges in between. In some embodiments, the effective amount of UVA is about 13 J/cm$^2$. In some embodiments, the effective amount of UVA is about 26 J/cm$^2$.

The currently accepted MED (minimal erythema dose), generally understood to be a threshold dose that can cause sunburn, is about 15 J/cm$^2$. This equates to roughly 45 minutes of continuous sun exposure, or about 45 minutes of continuous exposure in typical tanning beds. Humans have some tolerance of pulsed exposure. There can be at least two approaches to determine the minimum dose for biological application: one, to determine how much infection reduction occurs from 45 minutes of applying a effective amount of UVA; or two, do skin tests to see if an effective pulsed technique causes any erythema.

In some embodiments, the effective amount of UVA can be deposited, via continuous delivery, or pulsed delivery, or both, over a time period of about 6 hours, about 8 hours, about 12 hours, about 16 hours, about 20 hours, about 24 hours, about 28 hours, about 32 hours, including all values and sub ranges in between.

During use of a system and/or apparatus as disclosed herein, upon activation (i.e., as the control circuit board is activated), the UVA light source will emit UVA wavelength radiation on to the elected surface (e.g., a wound, or a medical device) for a preset duration calculated to be adequate to obtain a target reduction in growth of microorganisms. In some embodiments, the system and/or apparatus will automatically stop irradiating the surface when the preset duration is complete. In other embodiments, the system and/or apparatus will repeat the process of emitting UVA wavelength radiation on to the elected surface for the preset duration, such as, for example, until the system and/or apparatus is powered off and/or removed from the site. The amount/effective amount of UV light required can depend on several variables including distance to site, target site composition (natural or synthetic), humidity, temperature, and aeration, and can be predetermined (e.g., programmed into the circuit board), determined manually (e.g., calculated and entered by a user into an interface associated with the system and/or apparatus), and/or automatically (e.g., via one or more sensors associated with the system and/or apparatus). Once deployed, the system and/or apparatus can require minimal monitoring.

EXAMPLE 1

The currently accepted MED (minimal erythema dose), generally understood to be a threshold dose that can cause sunburn, is about 15 J/cm$^2$. This equates to roughly 45 minutes of continuous sun exposure, or about 45 minutes of continuous exposure in typical tanning beds. Humans have some tolerance of pulsed exposure. There can be at least two approaches to determine the minimum dose for biological application: one, to determine how much infection reduction occurs from 45 minutes of applying a effective amount of UVA; or two, do skin tests to see if an effective pulsed technique causes any erythema. As a comparison, the measured fluence of UVA spectrum from the sun is approximately 6.3 mW/cm² (Lowe, N. J. *Sunscreens: Development: Evaluation, and Regulatory Aspects: Second Edition.* Exposures of one hour or less of sunlight equivalent (e.g., In reality, the dose reaching the bacteria can be less (here, there was approximately 10% absorption by agar before UVA light reaches the surface).

Figure 2:
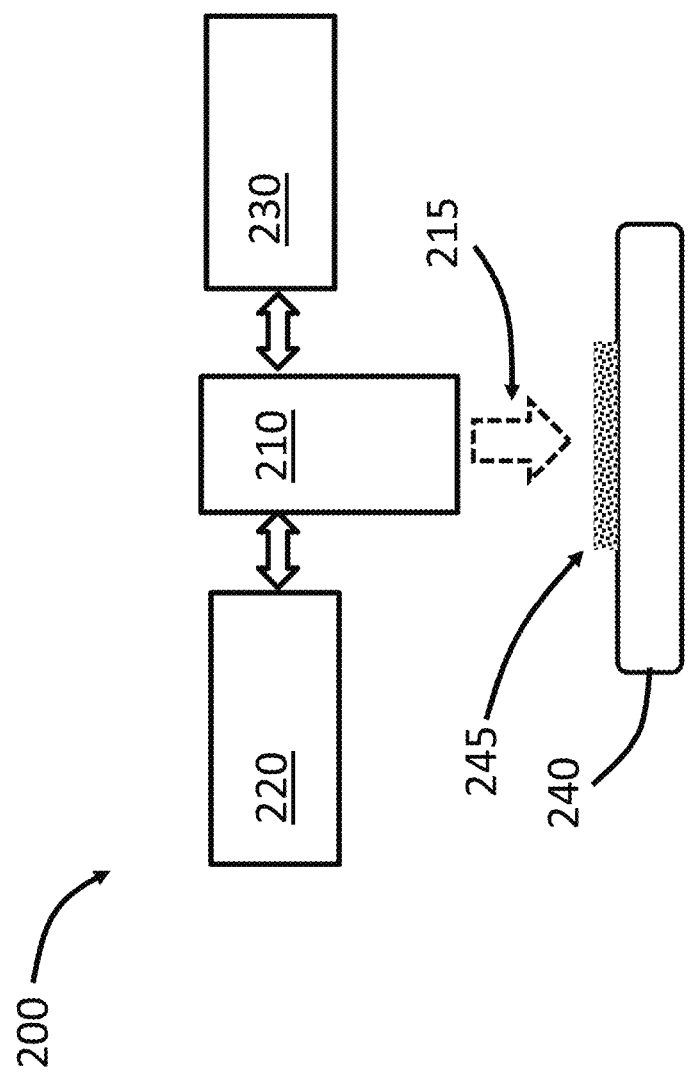
FIG. 2 shows a schematic of a system using UVA light for reducing pathogenic growth, according to embodiments.

FIG. 2 shows a schematic of an example system 200 using UVA light to reduce pathogenic growth, according to embodiments. The system 200 includes a UVA light source 210 to emit UVA light 215 toward a target area 240 that may have pathogens 245 on, near, or below the surface. The UVA light source is powered by a power source 220. A controller 230 is operably coupled to the UVA light source to control the operation of the UVA light source 210, including, for example, controlling one or more of the output energy, output power, output intensity, pulse duration (when in pulsed mode), repetition rate of the output pulses, and/or the like. In some embodiments, the controller 230 is programmable and/or configurable, by a user or another device (not shown), with a treatment regimen, and the controller is configured to control the operation of the UVA light source 210 based on the treatment regimen.

In one example, the UVA light source 210 includes one or more (light emitting) diodes, which can be based on gallium nitride (GaN). The light emitting diodes can be a single diode, multiple diodes, a row of diodes, an array of diodes, and/or the like. Each diode in any multi-diode arrangement can emit light at the same wavelength or different wavelengths. For example, different diodes in an array of diodes can be tuned (e.g., via temperature control or electric current control) to emit light at different wavelengths. (if needed, also re-iterate that not all need to be turned on and off at the same time).

In another example, the UVA light source 210 can include solid-state bulk lasers, the lasing medium of which can be, for example, cerium-doped crystals such as $Ce^{3+}$:LiCAF or $Ce^{3+}$:LiLuF4. Cerium lasers can be pumped with nanosecond pulses from a frequency-quadrupled Q-switched laser, and can emit nanosecond pulses themselves. With Q-switched microchip lasers, even sub-nanosecond pulse durations are possible. Mode-locked operation can also be employed. In yet another example, the UVA light source 210 can include fiber lasers such as neodymium-doped fluoride fibers, which can emit light at around 380 nm. In yet another example, the UVA light source 210 can include dye lasers emitting light within the UVA region. In yet another example, the UVA light source 210 can include excimer lasers emitting nanosecond pulses. Example wavelengths can be between about 157 nm (F2) and about 351 nm (XeF), including all values and sub ranges in between.

In yet another example, the UVA light source 210 can include argon ion lasers, which can continuously emit light at wavelengths of about 334 nm and 351 nm. Some other ultraviolet lines are accessible with krypton ion lasers.

In yet another example, the UVA light source 210 can include nitrogen lasers, which are molecular gas lasers emitting in the ultraviolet. The strongest emission line is at 337.1 nm. In yet another example, the UVA light source 210 can include a laser with a longer wavelength (e.g., in the visible or near-infrared spectral region) and one or several nonlinear crystals for nonlinear frequency conversion. For example, the wavelength of 355 nm can be generated by frequency tripling the output of a 1064-nm Nd:YAG or Nd:$YVO_4$ laser, and 266-nm light is obtained with two subsequent frequency doublers, which in effect quadruple the laser frequency.

In one example, the UVA light source 210 can include a broadband light source emitting light at more than one wavelength. In another example, the UVA light source 210 can include narrow band light sources emitting lights substantially at a single wavelength (e.g., a laser).

In one example, the UVA light source 210 can emit lights in the UVA range. In another example, an addition light source can be used to emit lights at other wavelengths. For example, an infrared (IR) light source can be used to emit IR light toward the target area 240, which can have healing effects on skin wounds.

In the system 200 shown in FIG. 2, the UVA light 215 is transmitted directly toward the target area 240. In some embodiments, other configurations are also possible. In one example, the UVA light 215 can be transmitted through fibers, waveguides, or other medium toward the target area 240. For example, a pliable fiber can be used to transmit the UVA light 215 such that the UVA light 215 can be flexibly directed toward any target area.

In another example, the UVA light 215 can transmit through a focusing element (e.g., a lens) before reaching the target area 240. The focusing element may increase the intensity (or power density) of the UVA light 215 so as to more effectively reduce pathogenic growth on the target area 240.

In yet another example, the UVA light 215 can transmit through a diffusing element or a scattering element before reaching the target area 240. The diffusing or scattering element can increase the size of the UVA light 215 so as to fit the UVA light 215 with the target area 240 having a dimension different than that of the UVA light 215.

The power source 220 of the system 200 can include a battery or a DC power adapter. In some embodiments, the power source can be less than about 5×3 inches (e.g., with a single LED as the UVA light source 210). In another example, further miniaturization can be achieved to make the device smaller, cheaper, and/or disposable.

In yet another example, the power source 220 can include an AC power supply through a transformer to yield the appropriate voltage and current to operate the UVA light source 210. In yet another example, the power source 220 can include other energy storage devices, including but are not limited to, a capacitor, a super-capacitor, a fuel cell, a superconducting magnetic energy storage (SMES), a flywheel energy storage, a hydraulic accumulator, or any other energy storage devices known in the art.

The controller 230 can include various types of controlling devices. In one example, the controller 230 includes a programmable board with multiple outputs to control, for example, individual LEDs in an array of LEDs.

In another example, the controller 230 can include a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, and/or files containing higher-level instructions that are executed by a computer using an interpreter. For example, embodiments may be implemented using C, Java, C++, MATLAB or other programming languages and/or other development tools.

The processors described herein can be any processors (e.g., a central processing unit (CPU), an application-specific integrated circuit (ASIC), and/or a field programmable gate array (FPGA)) configured to execute one or more instructions received from, for example, a memory. In some embodiments, at least one processor can be a Reduced Instruction Set computing (RISC) processor. Each processor can be in communication with a memory and/or a network card. In some embodiments, each processor can accordingly send information (e.g., data, instructions and/or network data packets) to and/or receive information from a memory and/or a network card.

The memory can be any memory (e.g., a RAM, a ROM, a hard disk drive, an optical drive, other removable media) configured to store information (e.g., one or more software applications, user account information, media, text, etc.). The memory can include one or more modules performing the functions described herein. In some embodiments, the functions described herein can be performed by any number of modules. For example, in some embodiments, the functions described herein can be performed by a single module.

In some embodiments, the system 200 can further includes a heat dissipation element (not shown) to reduce heat deposition onto the target area 240. In one example, the heat dissipation element can include a mechanical fan to improve air circulation around the target area 240 to as to reduce heat deposition. In another example, the heat dissipation element can include a heat sink disposed under or near the target area 240 so as to remove heat deposited on the target area 240. In yet another example, the heat dissipation element can include a flow of cold liquid (e.g., water) around the target area 240 so as to dissipate heat deposited on and/or near the target area 240.

EXAMPLE 2

Figure 3:
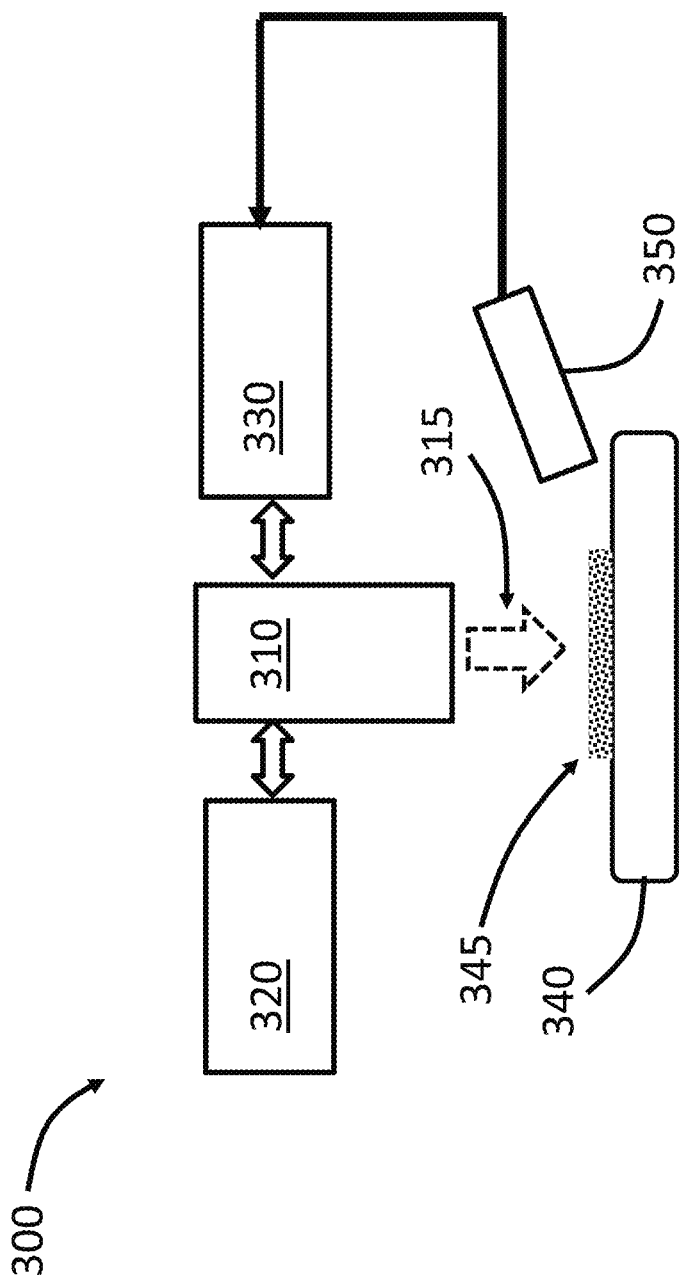
FIG. 3 shows a schematic of a UVA treatment system including feedback control, according to embodiments.

FIG. 3 shows a schematic of an example system 300 for UVA treatment using a feedback control, according to embodiments. The system 300 includes a UVA light source 310 powered by a power source 320 and controlled by a controller 330. The UVA light source 310 emits UVA light 315 toward a target area 340 so as to reduce growth of pathogens 345 on or near the surface of the target area 340. A sensor 350 can monitor the growth (or reduction) of the pathogens 345 and generates signals representing, for example, the number and/or density of the pathogens 345. The signals are transmitted to the controller 330, which can control the UVA light source 310, and the emitted UVA light 315 in turn, so as to more effectively reduce the growth of the pathogens 345.

For example, when the detected pathogens 345 are below a certain threshold, the signals generated by the sensor 350 can direct the controller 330 to turn off the UVA light source 310. In another example, when the detected pathogens 345 are above a threshold after a certain amount of time, the signals generated by the sensor 350 can instruct the controller 330 to increase the output power or intensity from the UVA light source 310. In yet another example, the sensor 350 may distinguish different types of pathogens and the generated signals can instruct the controller 330 to control the UVA light source 310 to emit different wavelengths of light so as to reduce different types of pathogens.

Various types of sensors can be used as the sensor 350. In some embodiments, the sensor 350 can include one or more optical biosensors which can have superior sensitivity, rapid detection, and good adaptability to a wide variety of assay conditions. The optical sensors can be either labeled or label-free, or combinations thereof.

In some embodiments, the sensor 350 can include a Surface Plasmon Resonance (SPR) sensor, which utilizes the oscillation phenomenon at the interface between any two materials to detect pathogens. SPR sensors can measure the refractive index near the sensor surface that may change as a result of interaction of target analyte in solution with bioreceptors on transducer surface. SPR can be used for real time monitoring of biochemical interactions of small analyte such as DNA hybridization, cell-ligand, protein-peptide, and protein-lipid. SPR sensors can also be modified to perform direct label-free detection of larger biomarkers such as bacterial pathogens.

In some embodiments, the sensor 350 can include bioluminescence sensors. Bioluminescence assays can be sensitive, rapid, and simple techniques for the quantitative detection of bacteria in samples by measuring the level of light emission from intercellular components. Bioluminescence sensing by the sensors 350 can be achieved by, for example, bacteria cell lysis to release interacellular components, followed by measurements using a bioluminescent reaction with luciferase.

In some embodiments, the sensor 350 can include fluorescent bioassay sensors, in which fluorescence-labeled bacteriophages can be used as staining agents for bacteria. The fluorescently stained bacteriophages can recognize and bind to their host bacteria. The complex of phage-bacteria can be detected using flow cytometry and/or epifluorescent filter technique.

In some embodiments, the sensor 350 can include quartz crystal microbalance (QCM) biosensors, which can be sensitive mass sensors with the capability for detection of nanogram changes in mass. A QCM sensor can be made of a thin piezoelectric plate coated on both sides with two metallic electrodes. The application of an electrical field across the quartz crystal can excites the mechanical resonance. The adsorption of mass onto the electrode surface can shift the resonance to lower frequencies. The rate of frequency change can be proportional to the adsorbed mass. Therefore, QCM sensors can be used to measure the mass of various target analytes by immobilizing specific probes on a sensor surface.

In some embodiments, the sensor 350 can include phage immobilized magnetoelastic sensors, which can oscillate mechanically when an AC magnetic field is applied. The resonance occurs when the frequency of the applied field equals to the natural frequency of sensors. The addition of non-magnetoelastic material (e.g., pathogens) to the sensor surface can dampen the mechanical oscillation, thereby shifting the resonance frequency to lower values. The response of the magnetoelastic sensors can be measured in the absence of direct physical wire contacts to the sensor, making the possibility of real time and in vivo bio-detection systems possible.

In some embodiments, the sensor 350 can include amperometric biosensors based on electrochemical detection of pathogens. Amperometric biosensors can include a reference electrode and a working electrode. A bias voltage can be applied to these electrodes to produce a current in the analyte. The current produced directly depends on the rate of electron transfer, which changes with variation in ionic concentration of analyte. Amperometry can detect ions in solution by measuring the changes in electric current.

In some embodiments, the sensor 350 can include impedimetric biosensors based on electrochemical impedance spectroscopy (EIS). EIS biosensors measure the changes in impedance over a range of frequencies that can occur as a result of biomolecular interaction. EIS biosensors can perform bacterial detection by monitoring the changes in the solution-electrode interface due to the capture of microorganisms on the sensor surface. The capture of target analyte such as bacteria on sensor usually increases the impedance due to the insulating properties. Bacteriophages can be used as a crosslinkage between bacteria and electrode surface.

More information about sensors to monitor pathogens can be found in Singh, et al., Recent Advances in Bacteriophage Based Biosensors for Food-Borne Pathogen Detection, *Sensors,* 13, 1763-1786 (2013), and Lazcka et al., Pathogen detection: A perspective of traditional methods and biosensors, *Biosensors and Bioelectronics,* 22, 1205-1217 (2007), the entire disclosures of both of which are incorporated herein by reference in their entireties.

It is understood that FIG. 3 shows a single sensor 350 for illustrative purposes only, and that more than one sensor, such as a sensor array, can be used to more accurately monitor the number of pathogens 345 on or near the target area 240.

In some embodiments, the UVA light source 310, the power source 320, and the controller 330 can be functionally and/or structurally similar to the UVA light source 210, the power source 220, and the controller 230 as described herein.

EXAMPLE 3

Figure 4:
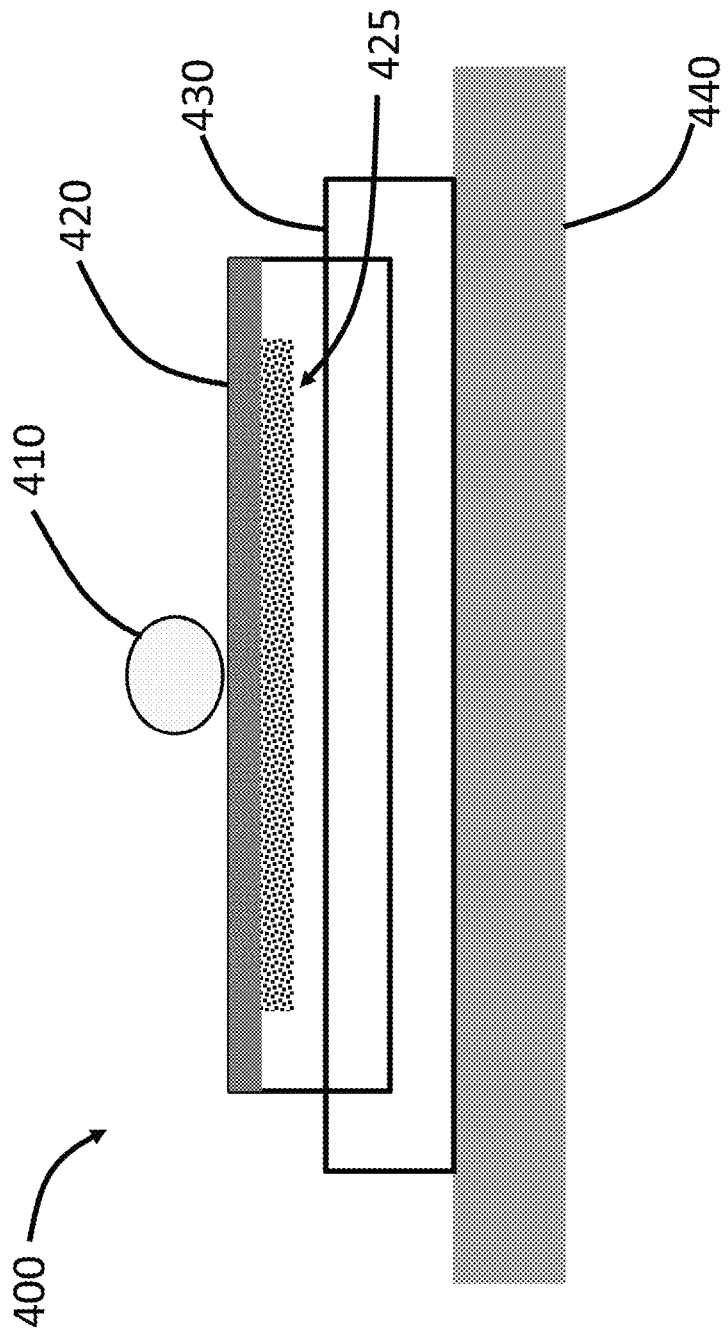
FIG. 4 shows a schematic of an in vitro system using UVA to reduce pathogen growth, according to embodiments.

FIG. 4 shows a schematic of an example in vitro system 400 to reduce pathogens, according to embodiments. The system 400 includes a sample holder in the form of an agar plate 420 that has been inoculated with skin flora 425. The agar plate 420 is disposed upside down to prevent heating of the bacteria of the skin flora 425. A constant temperature of 40 degrees Celsius is maintained by a heating element 440 disposed below a substrate 430 that supports the agar plate 420. The constant temperature can be maintained for about 2-4 days. A light source 410 is disposed in optical communication with the agar plate 420 and the pathogens 425 so as to control the growth of the pathogens 425. The light source 410 can include about one to three light emitting diodes (LEDs) of varying power to emit UVA light in the wavelength range of about 365-370 nm. Viewing angles of the LEDs can range between about 20-120 degrees.

The fluence for each LED can be evaluated independently of that reported by the manufacturer and measured to be between 1.8-3.6 mW/cm$^2$. As a comparison, the measured fluence of UVA spectrum from the sun is approximately 6.3 mW/cm$^2$ (Lowe, N. J. *Sunscreens: Development: Evaluation, and Regulatory Aspects: Second Edition,* (CRC Press, 1996; Pages 110-113, the entire disclosure of which is incorporated herein by reference in its entirety).

These values can be used to program the electronic component of the system to pulse the LED for a set duration. Variable doses can be used (e.g., ranging to match 1-4 hours of sunlight exposure). In some embodiments, the total output of UVA radiation should be kept as low as possible to minimize possible damage to healthy tissue. For example, Lowe showed significant damage after the equivalent of 4 hours of 'southern California' exposure.

About 26 J/cm$^2$, or about 2-3 hours of sun exposure, can substantially cease growth of bacteria colonies in the field of the viewing angle of the LED. Exposures of one hour or less of sunlight equivalent (e.g., about 8-13 J/cm$^2$) also can reduce bacterial colony count but to a lesser extent.

Since agar covering the petri dish has variable thickness, the maximum dose of UVA can be used to reach through the plastic plate and to calculate the exposure time duration. In reality, the dose reaching the bacteria can be less (here, there was approximately 10% absorption by agar before UVA light reaches the surface).

Figure 5:
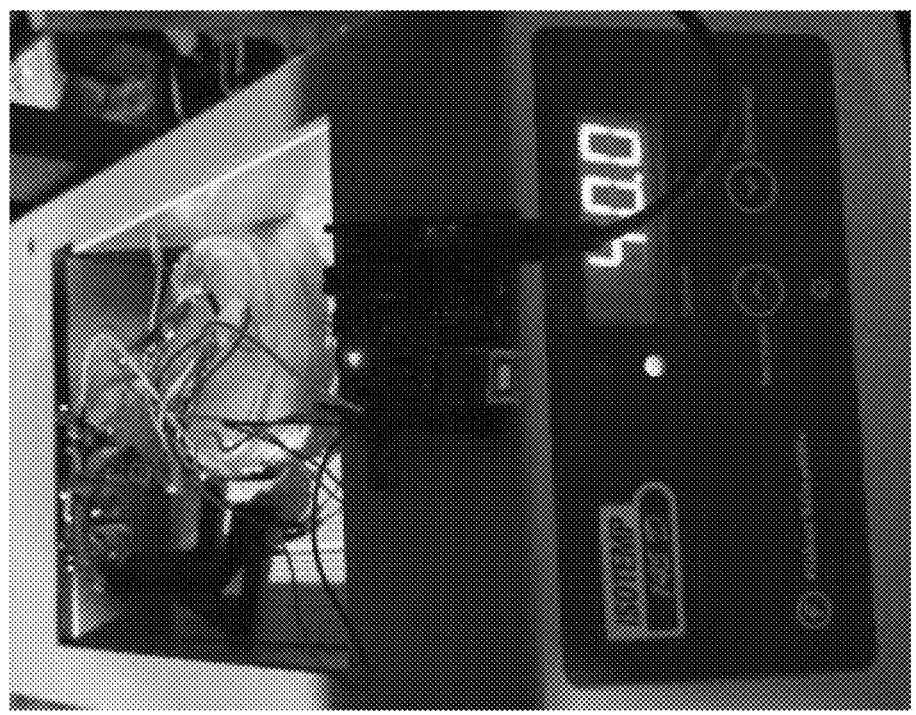
FIGS. 5-6 are photos of example in vitro systems using UVA to reduce pathogen growth, according to embodiments.
Figure 6:
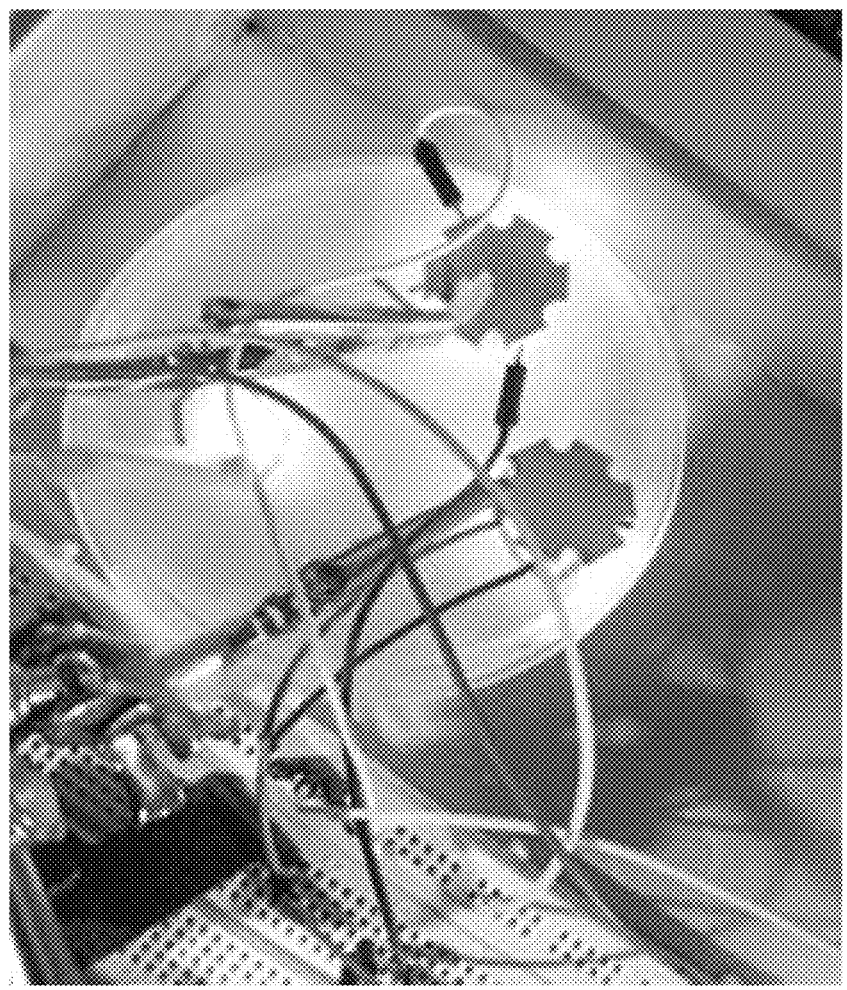

FIG. 5 and FIG. 6 are photos of example in vitro UVA treatment systems during use. FIG. 5 illustrates an overall environment of the example in vitro UVA treatment system, and shows temperature control at about 40 degrees Celsius. FIG. 6 illustrates illumination of the agar plate containing skin flora with three LEDs.

While various embodiments have been described above, it should be understood that they have been presented by way of example, and not limitation. Where methods described above indicate certain events occurring in certain order, the ordering of certain events can be modified. Additionally, certain of the events may be performed concurrently in a parallel process when possible, as well as performed sequentially as described above.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the technology disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of reducing pathogen growth on a target area, comprising:
    applying, to the target area, an effective amount from 1.5 mW/cm$^2$ to 11 mW/cm$^2$ of Ultraviolet-A (UVA) light for a duration from 45 minutes to 20 hours; and
    electronically monitoring a number of pathogens on the target area using a sensor which produces a signal representing the number and/or density of the pathogens detected.

2. The method of claim 1, wherein the applying of the effective amount of UVA light includes applying 3.6 mW/cm$^2$ of UVA light to the target area.

3. The method of claim 1, wherein the applying the effective amount of UVA light includes applying from 5 J/cm$^2$ to 26 J/cm$^2$ of UVA light to the target area.

4. The method of claim 1, wherein the applying of an effective amount of UVA light includes applying the UVA light for a duration from 6 hours to 20 hours.

5. The method of claim 4, wherein the applying of an effective amount of UVA light includes applying the UVA light for a duration from 10 hours to 20 hours.

6. The method of claim 1, wherein the applying of an effective amount of UVA light includes applying the UVA light in a pulsed manner.

7. The method of claim 1, wherein the applying of an effective amount of UVA light includes applying the UVA light in a wavelength range from 315 nm to 400 nm.

8. The method of claim 1 further comprising: automatically changing the effective amount of UVA light based on the number of pathogens detected on the target area.

9. A method of treating a condition, the condition including cellulitis, comprising: applying, to a target area, an effective amount from 1.5 mW/cm$^2$ to 11 mW/cm$^2$ of Ultraviolet-A (UVA) light for a duration from 45 minutes to 20 hours.

10. The method of claim 9, wherein the target area includes a skin defect.

11. The method of claim 9, further comprising: electronically monitoring a number of pathogens on the target area using a sensor which produces a signal representing the number and/or density of the pathogens detected.

12. The method of claim 11, further comprising: automatically changing the effective amount of UVA light based at least in part on the number of pathogens detected on the target area.

13. A method of sterilizing a target, wherein the target includes at least one of a skin surface, a surgical instrument, a central venous catheter, an intravenous line (IV), and a wound dressing, comprising: applying, to the target, an effective amount from 1.5 mW/cm$^2$ to 11 mW/cm$^2$ of Ultraviolet-A (UVA) light for a duration from 45 minutes to 20 hours.

14. The method of claim 13, further comprising: electronically monitoring a number of pathogens on the target using a sensor which produces a signal representing the number and/or density of the pathogens detected.

15. The method of claim 14, further comprising: automatically changing the effective amount of UVA light based at least in part on the number of pathogens detected on the target.

* * * * *